US005676954A

United States Patent [19]
Brigham

[11] Patent Number: 5,676,954
[45] Date of Patent: Oct. 14, 1997

[54] METHOD OF IN VIVO DELIVERY OF FUNCTIONING FOREIGN GENES

[75] Inventor: Kenneth L. Brigham, Nashville, Tenn.

[73] Assignee: Vanderbilt University, Nashville, Tenn.

[21] Appl. No.: 437,213

[22] Filed: May 8, 1995

Related U.S. Application Data

[63] Continuation of Ser. No. 919,083, Jul. 23, 1992, which is a continuation of Ser. No. 678,027, Apr. 1, 1991, which is a continuation-in-part of Ser. No. 431,552, Nov. 3, 1989, abandoned.

[51] Int. Cl.$^6$ .................. C17N 15/00; A61K 9/127; C07H 21/02
[52] U.S. Cl. .................. 424/450; 536/23.1; 435/172.3
[58] Field of Search .................................. 424/450

[56] References Cited

U.S. PATENT DOCUMENTS

| 4,579,821 | 4/1986 | Palmiter et al. | 435/172.3 |
| 4,897,355 | 1/1990 | Eppstein et al. | 435/240.2 |
| 5,017,359 | 5/1991 | Nicolau et al. | 424/1.1 |

FOREIGN PATENT DOCUMENTS

| 0027662 | 10/1979 | European Pat. Off. |
| 8504880 | 11/1985 | WIPO |

OTHER PUBLICATIONS

Brigham et al., "Rapid Communications: In vivo Transfection of Murine Lungs with a Functioning Prokaryotic Gene Using a Liposome Vehicle", *The American Journal of the Medical Sciences* 298(4):278, 1989.
Chen-Yen Wang et al., *Proceedings of National Acad. of Sciences*, 84:7799–8174 (1987).
Claude Nicolau et al., *Proceedings of National Acad. of Sciences*, 80:901–1158 (1983).
G. Ciliberto, L. Dente, R. Cortese (1985) Cell 41, 531–540.
A.F. Russo, E.B. Crenshaw, III, S.A. Lira, D.M. Simmons, L.W. Swanson, M.G. Rosenfeld (1988) Neuron 1, 311–320.
C.M. Gorman, D. Gies, G. McCray, M. Huang (1989) Virology 171, 371–385.
R.M. Abra, C.A. Hunt, D.T. Lau (1984) Journal of Pharmaceutical Sciences 72, No. 2, 203–206.
Felger et al. PNAS 84:7413, 1987.
Pavlakes et al Recent Progess in Hormone Res. 39: 353, 1983.
Nicolau et al Meth in Enzymol. 149: 157, 1987.
Webster's dieting, 1986 defeterf "diste".
Palmiter et al Science 222: 809, 1983.
Giefton in *Testhol of Medicine* Mycology, Chapter 1, p. 3, 1991.
Guyton in *Textbook of Medical Physiology* Chapter 1, p. 3, 1991.
Telger et al PNAS 84: 7413, 1987.
Fidler et al Recent Resets in Cancer Research 75, 246, 1980 & Abstract.
Jorik et al. BBA 401: 336, 1975.
Pavlakis et al Recev Progress in Humane Res 39: 353, 1983.
Xhu et al. Science 261: 209, 1993.
Hauley Netsu et al. focus 15(3), 73, 1992.

*Primary Examiner*—Suzanne E. Ziska
*Attorney, Agent, or Firm*—Lyon & Lyon LLP

[57] ABSTRACT

A method of expressing a foreign gene in cells of a mammalian organ in vivo includes the step of injecting genetic material capable of inducing desired gene products into a mammal. The genetic material is complexed to cationic liposome carriers. The genetic material is lipofected into cells of the mammalian organ. Gene expression and cellular function of the genetic material are activated to produce the desired foreign products in the cells of the organ.

21 Claims, 7 Drawing Sheets

METHOD OF IN VIVO DELIVERY OF FUNCTIONING FOREIGN GENES

This application is a continuation of application Ser. No. 07/919,083, filed Jul. 23, 1992, now abandoned, which is a continuation of application Ser. No. 07/678,027, filed Apr. 1, 1991, now abandoned, which is a CIP of application Ser. No. 07/431,552 filed Nov. 3, 1989, now abandoned.

TECHNICAL FIELD

The present invention relates to the incorporation of a foreign gene into cells of a mammalian organ in vivo. More specifically, the present invention provides in vivo transient transfection of lung cells by intravenous injection of a genetic material.

BACKGROUND ART

Functioning DNA can be introduced by a variety of techniques resulting in either transient expression of the genes of interest, referred to as transient transfection, or permanent transformation of the host cells resulting from incorporation of the foreign DNA into the host genome. Berger, S. L., and A. R. Kimmel. 1987. "Guide to molecular cloning techniques". *Methods In Enzymology.* 152:692–694. Potter, H., L. Weir and P. Leder. 1984. "Enhancer-dependent expression of human K immunoglobulin genes introduced into mouse pre-B lymphocytes by electroporation". *Proc. Natl. Acad. Sci.* 81:7161–7165. Plasmids complexed with cationic liposomes, referred to as liposome-DNA complexes, have been used for the transfection of cell cultures.

The use of liposomes for such transfection has been referred to as lipofection. Of the many techniques used for transfecting cells, lipofection has been found to offer advantages of simplicity and high transfection efficiency. Brigham, K. K., B. Meyrick, B. Christman, L. C. Berry, and G. King. "Expression of a prokaryotic gene in cultured lung endothelial cells following lipofection with a plasmid vector". *Am J. Resp. Cell Mol. Biol.*, 1:95–100, 1989. Felgner, P. L., T. R. Gadek, M. Holm, R. Roman, H. W. Chan, M. Wenz, J. P. Northrop, G. M. Rignold, and M. Danielsen, 1987. "Lipofection: A highly efficient, lipid-mediated DNA-transfection procedure". *Proc. Natl. Acad. Sci.* 88:7413–7417.

Kaneda et al, Sci. Vol. 243, January 1989, pages 375–378 discloses an in vivo transfection technique wherein plasmid-DNA and nuclear protein were co-introduced into nondividing cells in rat liver by injection into the portal veins of adult rats, the plasmid-DNA being carried into liver cell nuclei by the nuclear protein. Wu et al in the *Journal of Biological Chemistry*, Vol. 263 No. 29 issue of October 15, pages 14621–14624, 1988 disclose an in vivo transfection technique wherein plasmids are bound to ligands for specific hepatic galactose receptor complexes injected IV and showed specific gene expression in the liver.

Nicolau et al., *Methods in Enzymology*, Vol. 149, pages 157–176, discloses the use of liposomes as carriers for in vivo gene transfer and expression. The Nicolau et al. disclosure requires great complexity and has limited usefulness. The Nicolau et al. method involves encapsulating DNA in large size liposomes. This requires that the DNA be included in the process of generating liposomes, a process which requires expertise in the methods for generating liposomes, special equipment for this process, while the process does not readily permit preparation of the encapsulated DNA. The reference demonstrates expression only in the liver and spleen with intravenous injection of liposome encapsulated DNA which would be expected since these large complexes would be taken up mainly by the reticuloendothelial system (e.g. Kupfer cells in the liver) and this is demonstrated in the disclosure. This limits the method to organs with a high proportion of reticuloendothelial cells, mainly the liver and spleen, regardless of the cite of injection or introduction into the system. Utilizing the Nicolau et al. method, there could be obtained some increase in liver endothelial and hepatocyte distribution by altering the membrane characteristics of the large liposome to target it to specific endocytic receptors, but this would limit the specificity of cell transfection to the specificity of the receptors chosen as the target. When the liposomes are injected intravenously pursuant to the Nicolau et al. reference, the reference discloses expression only in the liver and the spleen. Further, a possible additional problem with the approach of Nicolau et al. has to do with the possibility of toxicity of the injected material. Large liposomes are more likely to cause disturbances of hemodynamics and cells in the microcirculation due to their size.

The present invention provides an in vivo lipofection technique utilizing small liposome-DNA complexes which can be intravenously injected and which also can provide a possibility for targeting specific organs, unlike those methods disclosed in the prior art.

SUMMARY OF THE INVENTION

In accordance with the present invention, there is provided a method of expressing a foreign gene in cells of a mammalian organ in vivo, the method including the steps of injecting a gene expression inducer of desired gene products into a mammal. The inducer is complexed to a cationic liposome carrier. The inducer is lipofected into cells of the mammalian organ. Gene expression and cellular function of the inducer is activated to produce the desired gene products in the cells of the organ.

FIGURES IN THE DRAWINGS

Other advantages of the present invention will be readily appreciated as the same becomes better understood by reference to the following detailed description when considered in connection with the accompanying drawings wherein:

FIG. 1 shows expression of a human growth hormone gene in the lungs of mice following intravenous injection of a plasmid containing the coding region for human growth hormone driven by a metallothionein promoter. Data are expressed as ng hGH per 24 hours per gm tissue and all points are means of data from two different animals. Control values were subtracted from data in the figure. There was minimal expression of the foreign gene in either kidneys or liver, but the gene was expressed in the lungs with a time course similar to that seen in cultured endothelial cells;

DETAILED DESCRIPTION OF THE INVENTION

Figure 1:
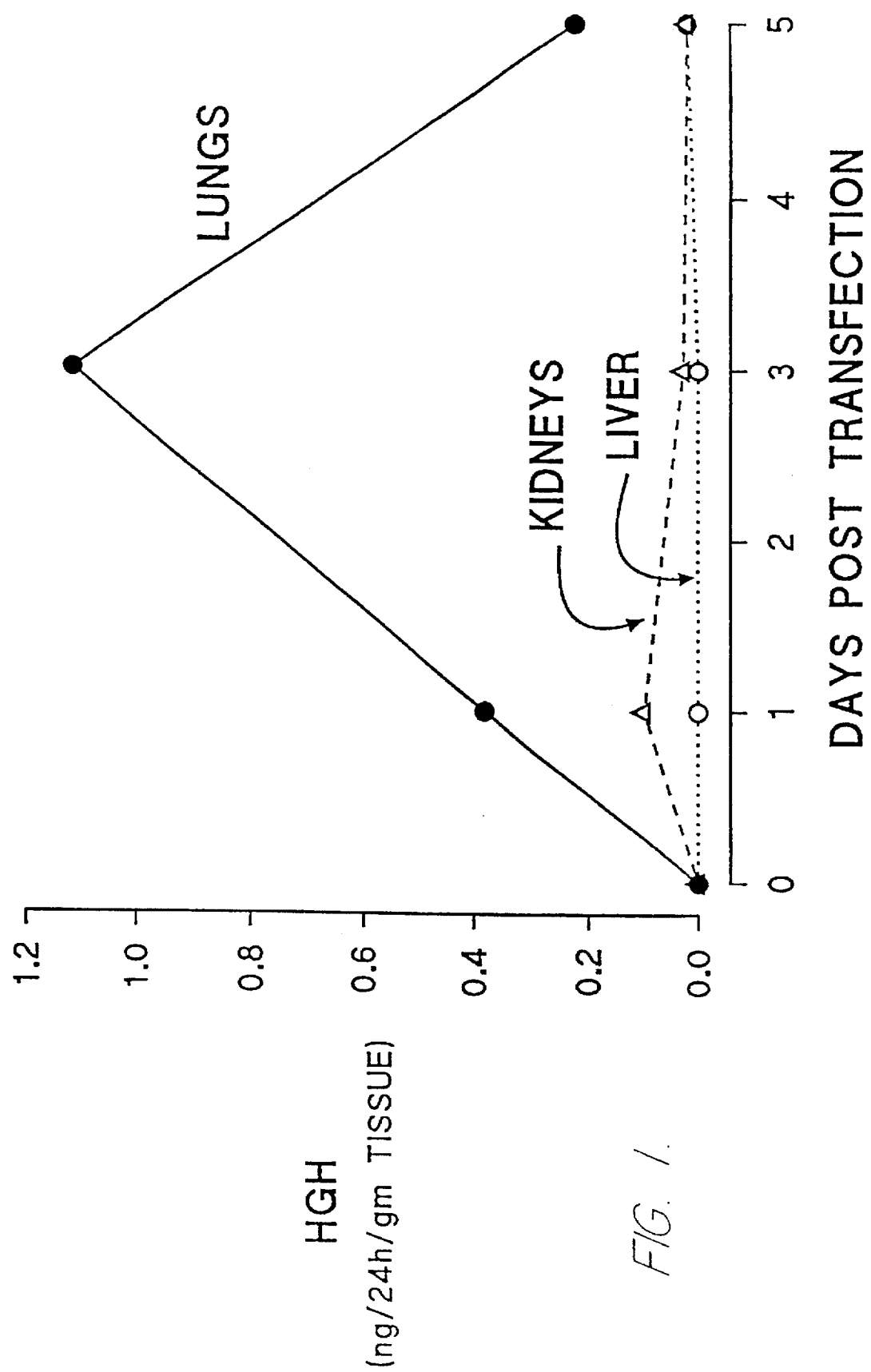

Generally, the present invention provides a method of expressing a foreign gene in cells of a mammalian organ in vivo. The method includes the steps of injecting a gene expression inducer of desired gene products into a mammal. For example, the gene expression inducer could be genetic material, such as DNA or RNA. The gene products could be, for example, a polypeptide or protein such as growth hormone.

The inducer is complexed to a cationic liposome carrier. An example of such a carrier is LIPOFECTIN~, manufactured by Bethesda Research Laboratories Life Technologies, Inc. of Gaithersburg Md. LIPOFECTIN~ reagent has previously been used for transfecting cells in vitro. LIPOFECTIN~ reagent contains the cationic lipid LN-[1-(2,3-Dioleyloxy)propyl]-N,N,N-trimethylammonium chloride which complexes with DNA by ionic interaction. Generally, the complex then fuses with cell membrane and is transfected into the cell. Methods of utilizing lipofection as a highly efficient transfection procedure have been reported by Felgner et al., *Proc. Natl. Acad. U.S.A.* Vol. 84, pages 7413–7417 November 1987; and by Felgner et al *Nature* Vol. 337 26 January 1989, pages 387–388.

Cationic liposome carriers such those disclosed above are relatively small. As discussed in detail in the experimental data section herein, the genetic material, such as DNA or RNA, is complexed to the cationic liposome carrier by simply incubating the small positively charged unilamellar liposomes with DNA at room temperature. The liposomes are stable for long periods of time. During the incubation, the liposomes surround the DNA or other genetic material, thereby creating a DNA-liposome complex held together ionic forces. This preparation requires no expertise in the preparation of liposomes and no special equipment, as does prior art methods discussed in the Background Art Section. In addition, the solutions can be maintained sterile for injection much more easily than those requiring simultaneous preparation of the liposomes and the DNA-liposome encapsulation, such as disclosed in the Nicolau et al. reference.

Utilizing the cationic liposome carrier, the genetic material is liopfected into the cells of the mammalian organ. Gene expression and cellular function of the genetic material is activated to produce the desired foreign products in the cells of the organ. That is, expression of particular expression vectors of the genetic material can be promoted.

More specifically, plasmid bound to the carrier, the plasmid containing the predetermined genetic material, is intravenously injected into the blood stream of the mammal in proximity to the organ for transfection. It has been found that when such plasmid carrier complexes are injected intratracheally, a high degree of transfection occurs in the cells of the lung. The genetic expression is transient. The transient expression in vivo of the transfected gene provides utility for gene therapy, including prevention and treatment of acute or subacute conditions which are not necessarily related to any genetic abnormality. The acute abnormality could be eradicated by the transient treatment, prolonged treatment not being necessary. Hence, the present invention could be used not only as a tool for correcting genetic abnormalities, but also as a new category of therapy which could broadly be applicable to human disease states. Accordingly, there is an advantage to the transiency of the plasmid transfection.

As the following experimental data shows, the present invention allows for targeting of specific organs. The following data shows that injection of the small liposome-DNA complexes made in accordance with the present invention intravenously produced expression mainly in the lungs (the proximal organ to injection) and, in some cases, lesser expression in systemic organs. Thus, the fundamental difference between the present invention and prior art methods is that the present invention results in maximal gene expression in the organ most proximal to the site of injection and thus provides the possibility for targeting which is unlike that possible with prior art methods. Further, the small liposome-DNA complexes of the present invention cause less physiological disturbances than the large liposomes utilized by the prior art.

Experimental Data

1. Expression of Coding Region for Human Growth Hormone

Methods

Plasmid Descriptions

Plasmid constructs obtained from Nichols Institute Diagnostics, San Juan Capistrano, Calif., were used. The plasmid PXGH5, was 6.7 kilobase construct in pUC12 containing the coding region for human growth hormone driven by a mouse metallothionein (mMT-1) promoter. Plasmid DNA was propagated in *Escherichia coil*. Plasmid DNA was isolated by alkaline lysis and purified by isopyknic equilibration gradient centrifugation in cesium chloride and ethidium bromide. Maniatis, T., E. F. Fritsch, and J. Sambrook. 1982. Molecular Cloning. A Laboratory Manual. Cold Spring Harbor: Cold Spring Harbor Laboratory.

In vivo Transfection

In a first study, in vivo studies were carried out in 6 week old specific pathogen free International Cancer Research/ Harlan Sprague-Dawley female mice (body weight 20–25 gm). Beginning 24 hours prior to DNA injection and continuing to the end of the experiment, all mice were given 5000 ppm $ZnSo_4$ in their drinking water. This amount of zinc has been shown to activate the metallothionein promoter in transgenic mice. Palmiter, R. D., R. L. Brinster, R. E. Hammer, M. E. Trumbauer, M. G. Rosenfeld, N. C. Birnberg, and R. M. Evans. 1982. Dramatic growth of mice that develop from eggs microinjected with metallothionein-growth hormone fusion genes. *Nature* 300:611–615. Each mouse was injected intravenously through a tail vein puncture with a 25 gauge needle with 30 µg pXGH5 DNA complexed to 150 µg liposome (Lipofection TM) in a total volume of 30 µl. Mice were killed 1, 3 and 5 days following DNA injection by an intraperitoneal injection of pentobarbital and the lungs, liver and kidneys were removed under sterile conditions. The organs were weighed, minced and placed in 60 mm Petri dishes to which were added 2 ml medium 199. The dishes were incubated for 24 hours at 37° C. in 5% $CO_2$ after which the contents were centrifuged and growth hormone assays were performed on the medium. Growth hormone production was calculated as the product of hGH concentration and the total volume of medium (2 ml), normalized to organ weight and expressed as ng hGH per gm tissue per 24 hours. Identical measurements were made in 5 nontransfected control mice.

2. Results

In vivo Transfection

Medium from 24 hour incubations of lungs, liver and kidneys removed from mice which were not injected with the plasmid-liposome complex showed very low levels of immunoreactive hGH. Calculated hGH production in ng per gm tissue per 24 hours was: lungs=0.26; kidneys=0.26; liver=0.06 (mean of n=5 in all cases). Expression of the hGH gene in mouse organs removed at different intervals following intravenous injection of plasmid-liposome complex is shown in FIG. 1. There was little production of growth hormone by either kidneys or liver. However, lungs removed from the transfected mice produced substantial amounts of growth hormone. hGH production was increased by 24 hours after injection, peaked at 3 days after injection and by 5 days was declining. This time course is similar to that seen in cultured endothelial cells.

3. Experiment 2

A plasmid which contained a prokaryotic (bacterial) gene, chloramphenicol acetyltransferase (CAT), was bound to LIPOFECTIN~ reagent. The liposome-DNA complex was injected into mice. The lungs of the mice were shown to express CAT gene. CAT is not present in any mammalian cells normally and measurement of CAT activity is thus an absolute index of successful expression of the gene. Previously, this plasmid construct was commonly used in cultured cells where CAT activity is proportional to mRNA levels.

Figure 2:
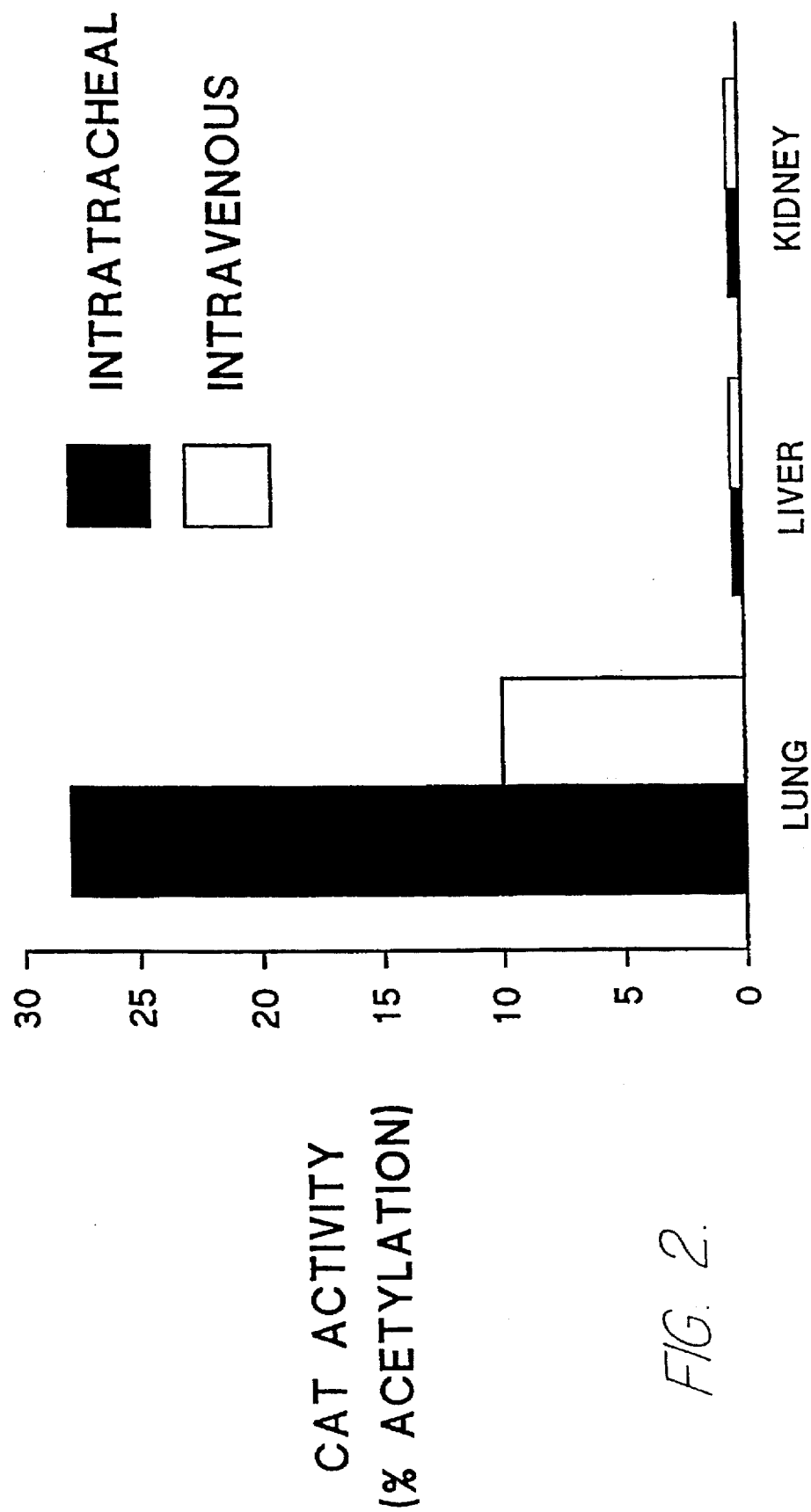
FIG. 2 shows CAT activity in the organs of mice 72 hours following injection of the DNA-liposome complex.
Figure 3:
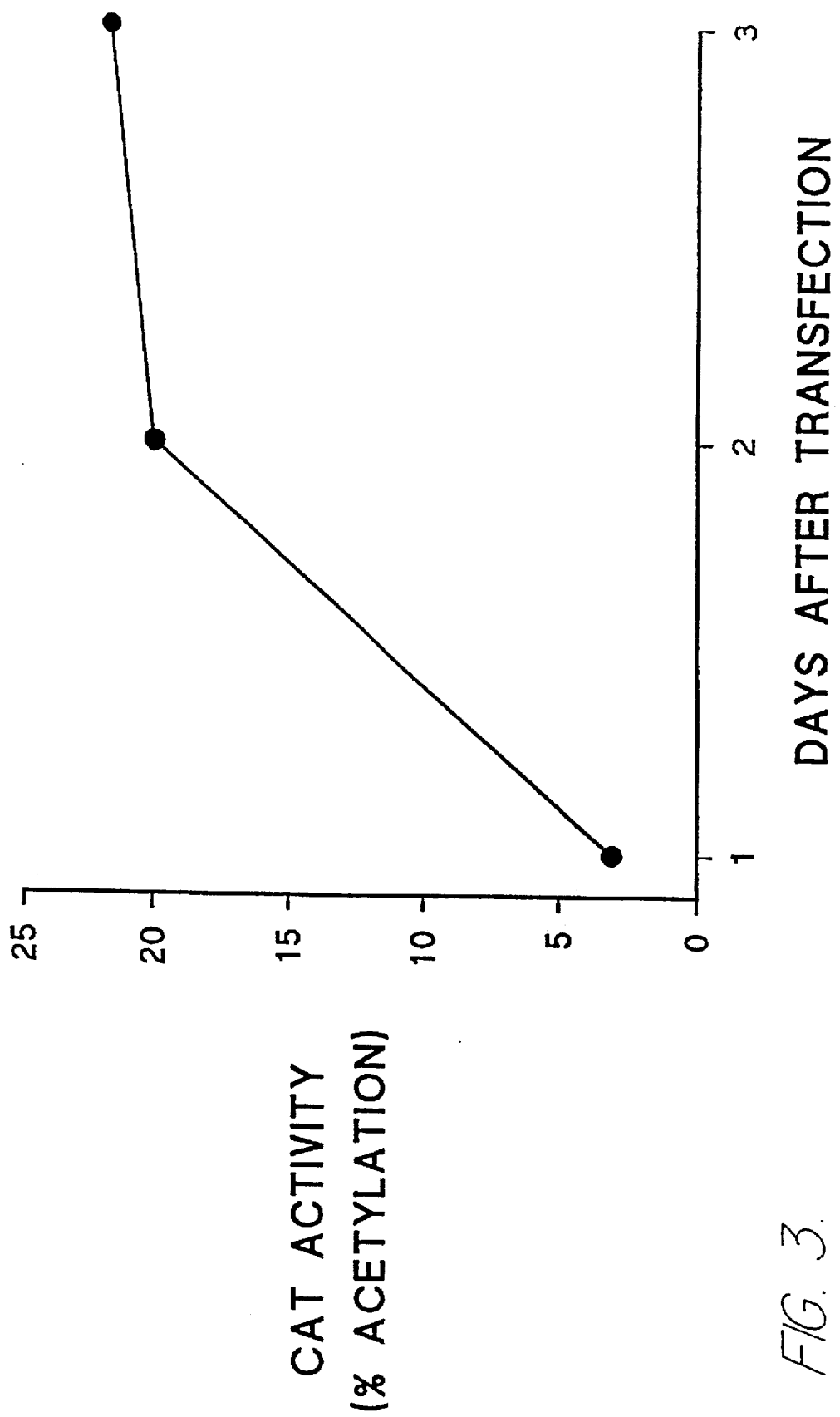
FIG. 3 shows lung CAT activity for the 3 days following injection of the liposome-DNA complex.

FIG. 2 shows CAT activity in the organs of mice 72 hours following injection of the DNA-liposome complex and FIG. 3 shows lung CAT activity for the three days following intravenous injection of the liposome-DNA complex. There is a large amount of activity in the lungs with no detectable activity in peripheral organs. It is expected that the specific transfection of the lungs is probably because of the lungs being the first organ distal to the site of injection. When the DNA-liposome complex is given intratracheally, as indicated in the Figure, larger amounts of activity appear in the lungs than with intravenous studies. Intraperitoneal injection show no CAT activity in any organ up to 6 days following injection.

4. Experiment 3

Mice were injected intravenously through a tail vein with either a plasmid containing the coding region for human growth hormone (HGH) driven by a metallothionein promoter complexed to liposomes, the DNA alone or the liposomes alone. All of the animals were given $ZnOSO_4$ in their drinking water beginning 24 hours prior to injection. These experiments are identical to experiments discussed above except that these experiments include additional relevant controls. The animals were killed two days following the injection. The organs were harvested and incubated for 24 hours in medium 199. Human growth hormone was measured in the medium using an immunoassay specific for human growth hormone.

Figure 4:
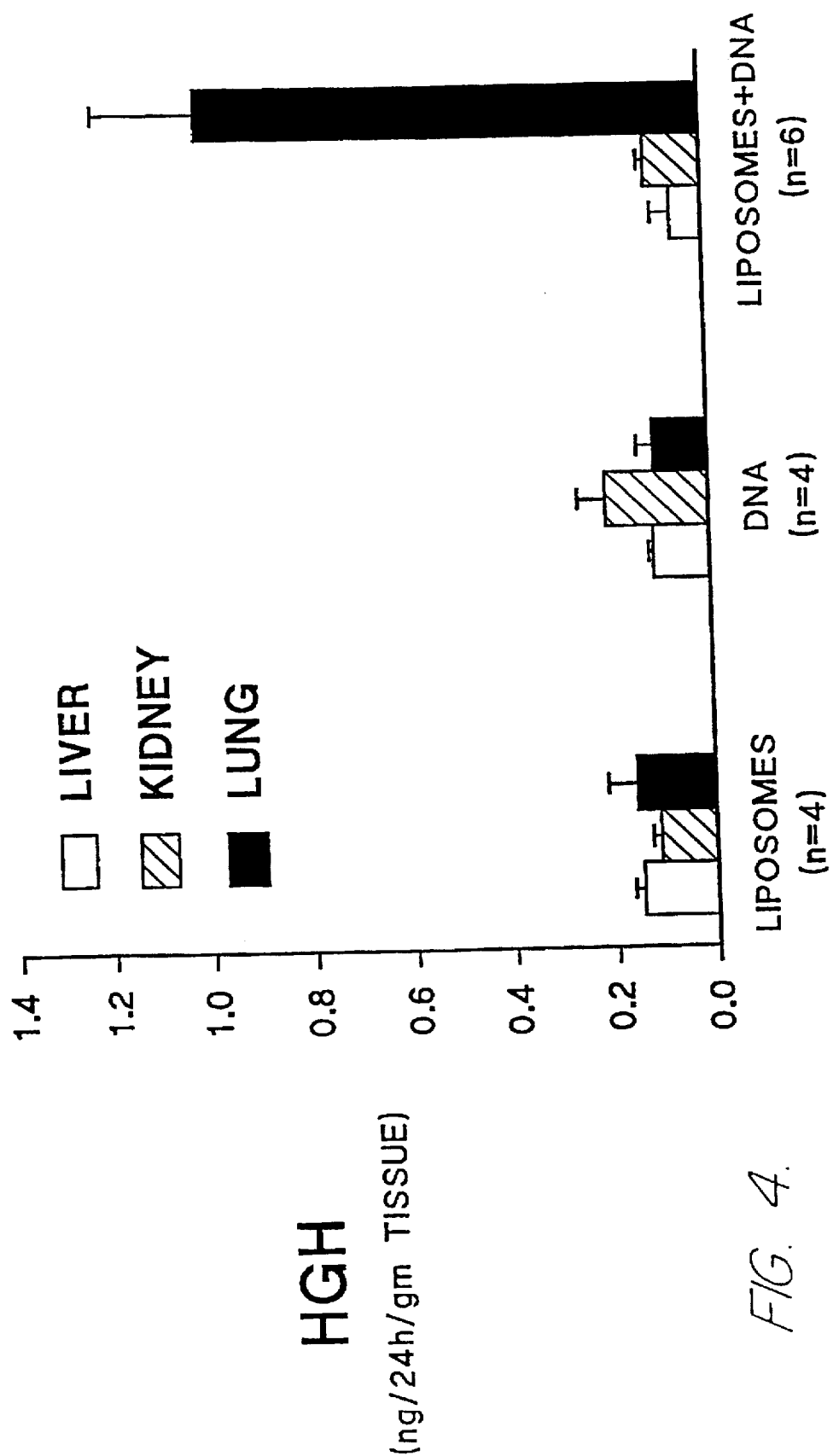
FIG. 4 is a graph showing intravenous transfection of murine tissues with predominant expression in the lungs.

As shown in FIG. 4. HGH was produced in substantial amounts by the lungs of the mice receiving the liposome-DNA complex. There was little signal in either the liver or kidneys from the same animals or in any of the organs harvested by the control groups of animals.

5. Experiment 4

Figure 5:
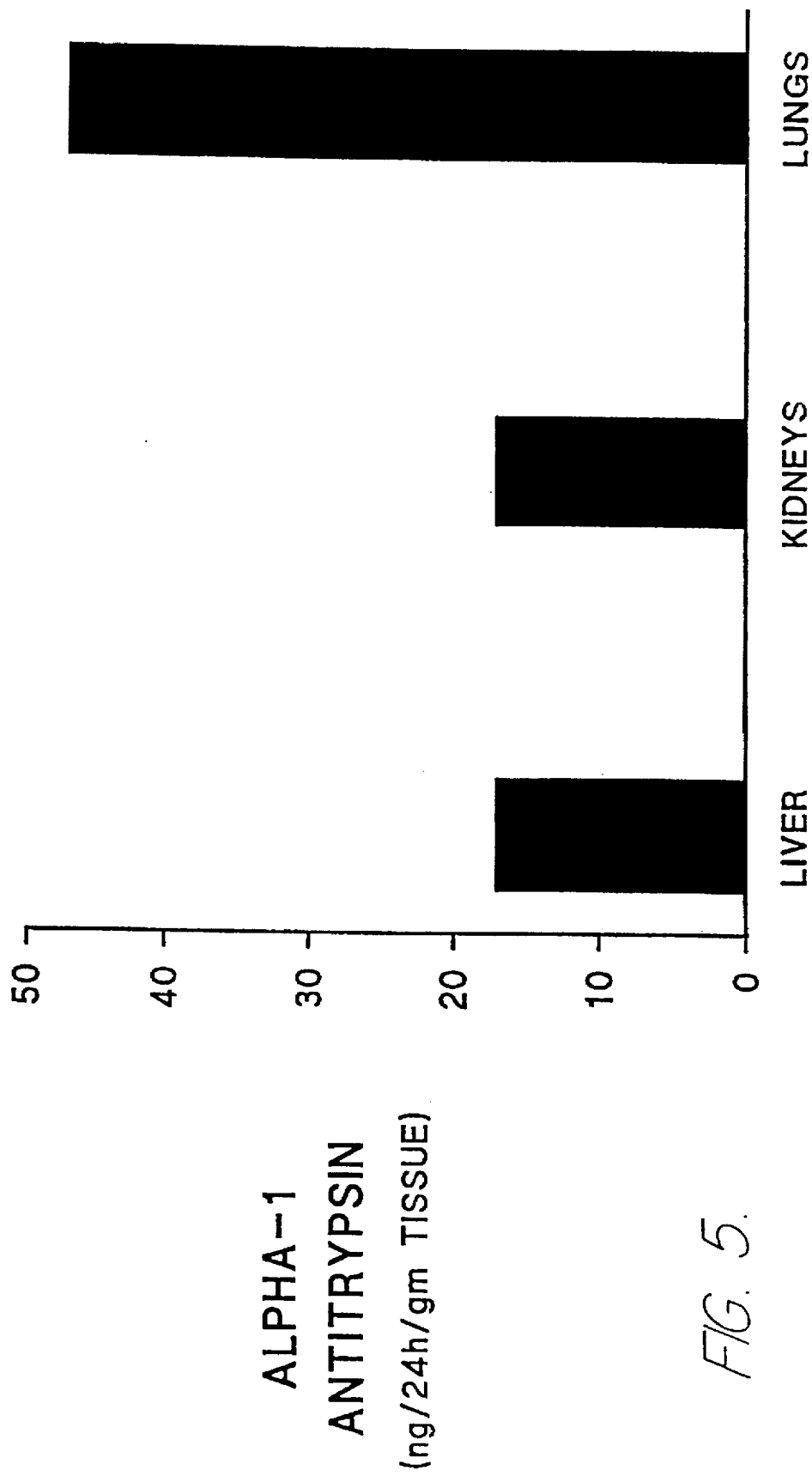
FIG. 5 is a graph showing expression of a human alpha-1 antitrypsin gene in the organs of a rabbit.

FIG. 5 shows the results of an experiment wherein production of α-1 antitrypsin was made by lungs, liver, and kidneys removed from a rabbit four days following intravenous injection of a plasmid containing the human α-1 antitrypsin coding region driven by a CMV promoter complexed to the same liposomes as used in the previously mentioned experiments. A control rabbit was injected at the same time with the same vector which did not contain the α-1 antitrypsin gene and the values in the graph have the control values subtracted from them prior to plotting. Animals were sacrificed four days following injection. The organs were harvested, the incubated organs minced for 24 hours in medium 199, and human α-1 antitrypsin was measured in the medium using an immunoassay specific for the human protein. Successful expression of the human gene is shown by substantial production of α-1 antitrypsin by the lungs with some minor production in the liver and kidneys as well.

6. Experiment 5

Figure 6:
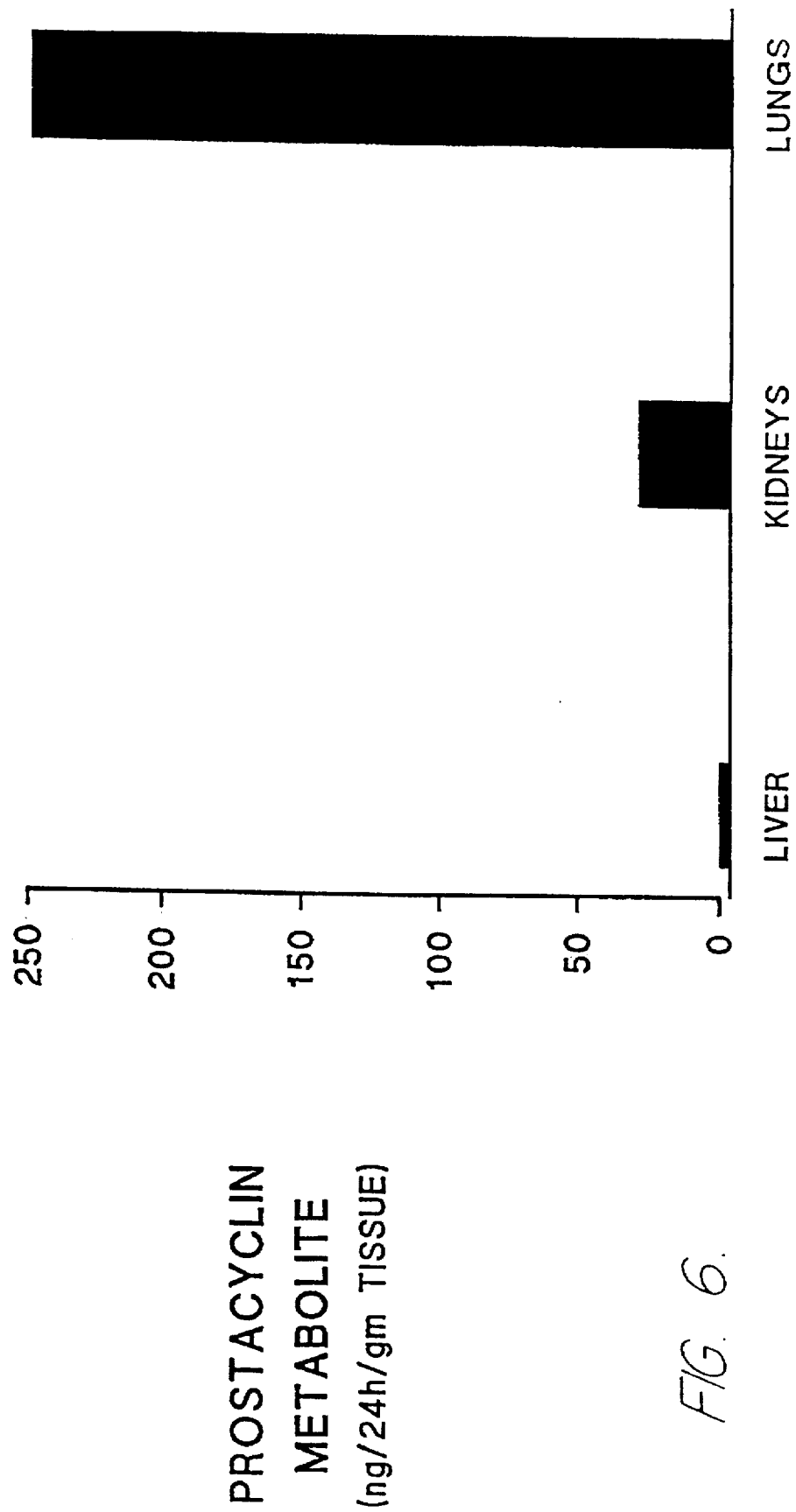
FIG. 6 is a graph showing expression of ovine PGH synthase genes in the organs of a rabbit.

FIG. 6 shows production of the endothelial derived prostanoid, prostacyclin, by organs removed from a rabbit four days following intravenous injection of a plasmid containing the coding region for ovine prostaglandin synthase driven by a CMV promoter complexed to the same liposome preparation as used in the previously described experiments. A control rabbit was injected at the same time with the same vector which did not contain the prostaglandin synthase gene and the values in the graph have these control values subtracted from them prior to plotting. As with the previously described experiments, the animals were sacrificed four days following injection. The organs were incubated after mincing for 24 hours and measured prostacyclin production was determined as the amount of the stable prostacyclin metabolite, 6-keto $PGF1\alpha$ in the medium. Successful expression of the prostaglandin synthase gene in the lungs was obtained and there was also some expression in the kidneys.

These data, in combination with those shown in FIG. 5, indicate that the principal transfection with the method described herein occurs in the organ most proximal to the site of injection, but that transfection can occur in both the lungs and systemic organs. The prostanoids produced by these studies were mainly prostacyclin and prostaglandin E2, both of which are derived from endothelium. These results suggest that endothelial cells are the main cell type targeted by this approach.

7. Experiment 6

Figure 7:
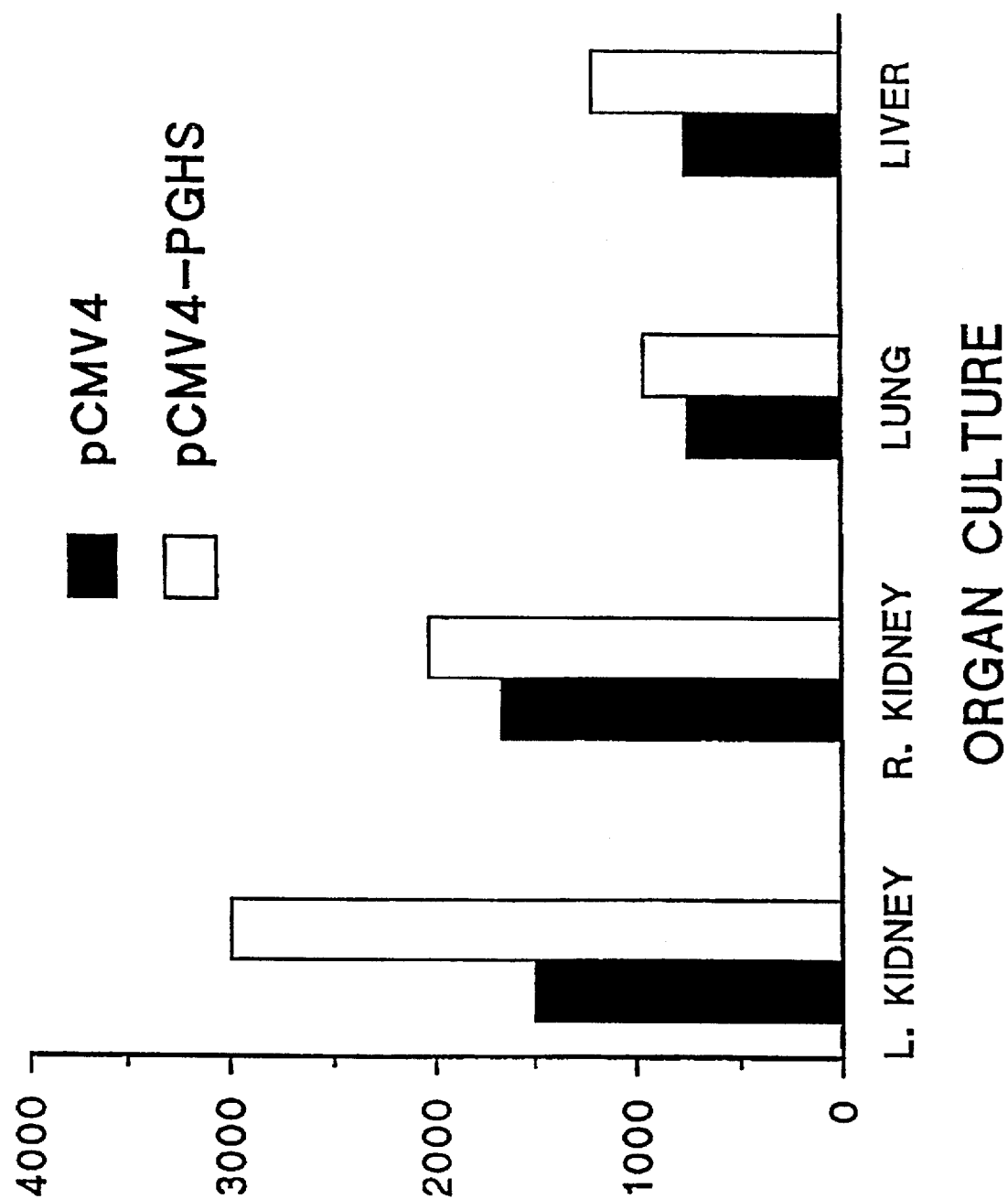
FIG. 7 is a graph showing in vivo lipofection of PGH synthase in rats.

In this experiment, rats had liposome complexes of either a DNA construct containing the prostalylandin synthense gene pCMV4-PGHs, or the same DNA without the gene (PCMV4), infused into the left renal artery directly. Animals were allowed to recover and 48 hours later they were killed, the organs removed, minced, and cultured for 24 hours. PGHS gene expression was measured as generation of the stable prostacyclin metabolite, 6-Keto PGFla, by the organ culture. As shown in FIG. 7, PGHS gene was expressed only in the directly transfected kidney, 6-Keto PGFla generation was the same in the untransfected (right) kidney in the experimental animals as in either kidney from control animals. Neither lung nor liver showed evidenced of expression of the transfected gene.

8. Experiment 7

This experiment demonstrates that DNA-liposome can be effectively delivered by an aerosol route and that it is possible to target subpopulations of lungs by choosing the route of administration.

More specifically, sections of lung from each of two rats were taken 24 hours after in vivo administration of a plasmid containing CMV promoter driven β-galactosidase gene complex to small cationic liposomes. One lung is from an animal which received DNA-liposome by breathing an aerosol. The other lung is from an animal which received the same dose of DNA-liposome intravenously by injection into the tail vein. The sections were stained for β-galactosidase activity which stains blue. The animal receiving DNA by aerosol (top picture of FIG. 8) shows expression of the β-galactosidase gene mainly in airway epitheilum whereas the animal receiving the DNA intravenously shows gene expression predominately in the lung parenchyma.

The above data demonstrates that the DNA liposome can effectively delivered by the aerosol route, as well as the intravenous route. Further, it shows that the selection of administration route can target subpopulations of lung cells.

9. Discussion

The present inventive method permits introduction of foreign genes directly into host cells by injection of the genetic material. DNA bound to specifically synthesized cationic liposomes can introduce plasmids and other gene vectors into cultured cells with high efficiency. It is suspected that the plasmid does not enter the host genome and does not replicate in a mammalian cell so that the gene expression is transient, in the present examples lasting for greater than a week.

Following intravenous injection of the DNA-liposome complex, the major expression of the gene was found in the lungs. This is interpreted to mean that the principal organ transfected following intravenous injection is the first capillary bed down stream from the injection site. Accordingly, it should be possible to selectively transfect organs by injecting the liposome DNA complex in the artery supplying the organ.

Previously, Iannuzzi and Associates transfected human airway epithelial cells with a plasmid containing the prokaryotic gene, CAT< driven by a SV40 promoter by electroporation. Iannuzzi, M. C., J. L. Weber, J. Yankaskas, R. Boucher, and F. S. Collins. 1988. "The introduction of biologically active foreign genes into human respiratory epithelial cells using electroporation". *AM. Rev. Resp. Dis.* 138:965–968. These experiments showed expression of the CAT gene in transfected cells. Swiebel and co-workers transformed rabbit aorta endothelial cells in culture by infecting them with a retrovial vector containing either hGH or adenosine deaminase coding regions driven by an SV40 promoter. Zwiebel, J. A., S. M. Freeman, P. W. Kantoff, K. Cornetta, U. S. Ryan, and W. F. Anderson. 1989. "High-level recombinant gene expression in rabbit endothelial cells transduced by retroviral vectors". *Science* 243:220–243. The experiment showed expression of the genes in the transformed cells which persisted through many generations in culture. The inventors of the present invention earlier showed that bovine lung endothelial cells could be transfected by lipofection at very high efficiency with a plasmid containing the CAT coding region driven by a Rous sarcoma virus promoter. Brigham, K. L., B. Meyrick, B. Christman, L. C. Berry, and G. King. "Expression of a prokaryotic gene in cultured lung endothelial cells following lipofection with a plasmid vector". *Am. J. Resp. Cell Mol. Biol.* 1:95–100, 1989.

The studies detailed above demonstrate the use of transfecting the lung of intact animals with a functioning gene encoding a physiologically relevant secreted human protein driven by the metallothioein promoter. The time course of expression of the transfected gene in the lung was similar to the time course of expression of the same gene in cultured lung endothelial cells (experiments not reported).

Gene therapy has generally been conceived as principally applicable to genetic deficiency diseases where permanent cure may be effected by introducing a functioning gene. Freiedmann, T. 1989. "Progress toward human gene therapy". *Science* 244:1275–1281. However, a much larger group of diseases might be treatable by transiently engineering host cells to produce beneficial proteins. For example, the intracellular enzymes, superoxide dismutase and catalase, may be crucial protectors of the lungs from oxidant injury and increased intracellular levels of these proteins might protect the lung from injury of a variety of causes. Transient increase in endothelial prostaglandin synthase resulting in increased production of prostacyclin and prostaglandin $E_2$ might be beneficial in several diseases. The secreted antiprotease, alpha-1 antitrypsin, may be important in the pathogenesis of emphysema and other lung diseases and genetic engineering of lung cells to produce this protein could be therapeutic in human disease states. Garver, R. I., J. F. Mornex, T. Nukiwa, M. Brantly, M. Courtney, J. P. CeCoco, and R. G. Crystal. 1986. "Alpha-1 antitrypsin genes". *N. Engl. J. Med.* 314:762–766. Numerous other theoretical possibilities could be suggested.

The present data demonstrate that lung cells in living animals can be engineered by transfection to express foreign genes encoding both intracellular and secreted proteins. Several promoters, including those which permit experimental control of gene expression, can be used to drive expression of the transfected gene. Use of plasmid vectors helps to assure transient expression of the gene. This approach will permit elucidation of molecular mechanisms effecting gene expression in specific lung cells and specific investigation of the rolls of various proteins in lung cell responses. In addition, in vivo transient transfection may make gene therapy applicable to a broad range of human diseases.

The experimental data further demonstrates that gene expression does not occur with either DNA alone or liposomes alone but that the DNA-liposome complex is essential. Experiments 5 and 6 specifically show that organ transfection with functioning foreign DNA is affected by intravenous injection of the DNA-liposome complex. The experiments show that the method crosses species lines effectively.

The experiments further show that intravenous injection of DNA-liposome complexes result in expression of the foreign gene in the lungs and, to a lesser extent, in the liver and kidneys in the case of the human alpha-1 antitrypsin gene and in the lungs and kidneys in the case of the ovine prostaglandin H synthase gene. In both cases, there is greater expression in the lungs which would be expected since this is the first organ traversed by the injected complexes, even though the data establishes that expression can be obtained to a much lesser degree in other organs as well.

The experiments further show that the DNA liposomes can be effectively delivered in an aerosol to the lungs. A second demonsion of the invention was also demonstrated by this experiment wherein it was shown that the route of administration makes it possible to target subpopulations of lung cells. That is, intravenous administration resulted in expression in a subpopulation of cells different from those cells targeted by the administration of DNA liposomes by the aerosol route.

Finally, the experimental results shown in FIG. 7 demonstrate specific organ targeting of in vivo gene transfection by choosing the site of lipisome-DNA injection. Further, this data demonstrates the applicability of the present invention in a further different species.

In summary, the experimental data herein shows an effective approach for expressing a foreign in cells of mammalian organs in vivo. The preparation of the liposome complexes used is simple and the use of the complex is potentially much less toxic than prior art methods. Finally, the present invention allows for targeting of organs for maximal effect of the cell transfection.

The invention has been described in an illustrative manner, and it is to be understood that the terminology which has been used is intended to be in the nature of words of description rather than of limitation.

Obviously, many modification s and variations of the present invention are possible in light of the above teachings. It is, therefore, to be understood that within the scope of the appended claims, the invention may be practiced otherwise than as specifically described.

What is claimed is:

1. A method of expressing a gene predominantly in a target organ in a mammal, comprising the step of:
    administering by injection a nucleic acid liposome complex capable of functionally expressing said gene to said mammal at a site whereby said target organ is the first organ having a capillary bed proximal to the site of administration,
    wherein said nucleic acid is complexed by ionic interaction to cationic liposomes that effect delivery of said gene predominantly to said target organ and transfect said gene into a cell in said target organ, and
    wherein said gene is predominantly expressed in said target organ.

2. The method of claim 1, wherein said target organ is the kidney and said administering step comprises injecting said nucleic acid liposome complex into blood afferent to the kidney.

3. The method of claim 1, wherein said target organ is the lungs and said administering step comprises administering said nucleic acid liposome complex into the trachea by aerosol administration.

4. The method of claim 1, wherein said target organ is the lungs and said administration step comprises injecting said nucleic acid liposome complex intravenously into the blood afferent to the lungs.

5. The method of claim 1, further comprising activating transient expression of the gene by administering an activator.

6. The method of claim 5, wherein the expression of said gene is controlled by a zinc-activated promoter and said activator is zinc.

7. The method of claim 6, wherein said coding region codes for human growth hormone.

8. The method of claim 6, wherein said zinc is administered by ingestion.

9. The method of claim 1, wherein said cationic liposome has the transfection characteristics of N-[1-(2,3-dioleyloxy)propyl]-N,N,N-trimethylammonium chloride.

10. A method of expressing a gene predominantly in the lungs in a mammal comprising the step of:
    administering by inhalation a plasmid capable of functionally expressing said gene to said mammal,
    wherein said plasmid is complexed by ionic interaction to cationic liposomes that effect delivery of said gene predominantly to said lungs and transfects said gene into a cell in said lungs, and
    wherein said gene is predominantly expressed in said lungs.

11. The method of claim 10, further comprising activating transient expression of said gene by administering an activator.

12. The method of claim 11, wherein the expression of said gene is controlled by a zinc-activated promoter and said activator is zinc.

13. The method of claim 12, wherein said coding region codes for human growth hormone.

14. The method of claim 12, wherein said zinc is administered by ingestion.

15. The method of claim 12, wherein said cationic liposome has the transfection characteristics of N-[1-(2,3-dioleyloxy)propyl]-N,N,N-trimethylammonium chloride.

16. A method of delivering a nucleic acid liposome complex predominantly to a target organ in a mammal, comprising the step of administering said nucleic acid liposome complex to said mammal by injection at a site whereby said target organ is the first organ having a capillary bed proximal to the site of administration,
    wherein said nucleic acid is complexed by ionic interaction to cationic liposomes that effect delivery of said nucleic acid predominantly to said target organ and transfect said nucleic acid into a cell in said target organ.

17. The method of claim 16, wherein said target organ is the kidney and said step of administering comprises injecting said nucleic acid liposome complex into the blood afferent to the kidney.

18. The method of claim 16, wherein said target organ is the lungs and said step of administering comprises administering said nucleic acid liposome complex into the trachea by aerosol administration.

19. The method of claim 16, wherein said target organ is the lungs and administration step comprises injecting the nucleic acid liposome complex intravenously into the blood afferent to the lungs.

20. The method of claim 16, wherein said cationic liposome has the transfection characteristics of N-[1-(2,3-dioleyloxy)propyl]-N,N,N-trimethylammonium chloride.

21. A method of delivering a nucleic acid predominantly to the lungs in a mammal, comprising the step of administering said nucleic acid by inhalation,
    wherein said nucleic acid is complexed by ionic interaction to one or more cationic liposomes that deliver said nucleic acid predominantly to said lungs and transfect said nucleic acid into a cell in said lungs.

* * * * *